United States Patent [19]

Alexander et al.

[11] Patent Number: 4,820,742
[45] Date of Patent: Apr. 11, 1989

[54] METHOD FOR CONTINUOUS MANUFACTURE OF SOLID WATER ABSORBING RESIN

[75] Inventors: William Alexander, Naperville, Ill.; Maynard Teppo, Fourche, S. Dak.

[73] Assignee: American Colloid Company, Arlington Heights, Ill.

[21] Appl. No.: 946,614

[22] Filed: Dec. 29, 1986

Related U.S. Application Data

[63] Continuation of Ser. No. 748,246, Jun. 24, 1985, abandoned.

[51] Int. Cl.$^4$ .......................... C08F 2/10; C08F 20/06
[52] U.S. Cl. ............................... 521/131; 521/109.1; 521/117; 521/149; 524/555; 524/827; 524/832; 526/75; 526/88; 526/240; 526/306
[58] Field of Search ............... 526/88, 173, 240, 306, 526/930, 75, 201; 524/555, 556, 827, 832; 521/149, 109.1, 117, 131

[56] References Cited

U.S. PATENT DOCUMENTS

| | | | |
|---|---|---|---|
| 4,283,517 | 8/1981 | Perricone et al. | 526/88 X |
| 4,525,527 | 6/1985 | Takeda et al. | 526/306 X |
| 4,530,979 | 7/1985 | Birch | 526/88 X |
| 4,552,938 | 11/1985 | Mikita et al. | 524/832 X |

Primary Examiner—Edward J. Smith
Assistant Examiner—F. M. Teskin
Attorney, Agent, or Firm—Mason, Kolehmainen, Rathburn & Wyss

[57] ABSTRACT

A method and apparatus for continuously manufacturing water absorbing resin. A mixed monomer solution is stored in a storage vessel and a polymerization initiator stored in an initiator storage vessel. The monomer solution is fed by gravity or otherwise through a conduit to a lower position (below the liquid surface) of a reaction chamber of a reaction vessel at a rate of, for example, 4 gallons per minute. Simultaneously, the polymerization initiator is fed at a rate of, for example, 0.2 gallons per minute by gravity or otherwise through a conduit to an opposite side of the reaction chamber, again at a lower portion (below a continuously maintained liquid level) to begin polymerization. The reaction product forms from an upper surface of the reactant mixture (mixed monomer solution plus initiator) and travels upwardly through a truncated frustoconical cone shaped upper portion of the reaction chamber as a solid resin. The reaction product is sufficiently rigid to proceed upwardly from an upper annular edge of the upper reaction chamber portion until the resin meets an upper conveyor belt. The upper conveyor belt, driven in a counterclockwise direction, pushes the mass of reaction product onto a lower conveyor belt on which the resin cures and dries without the addition of external heat.

6 Claims, 1 Drawing Sheet

U.S. Patent
Apr. 11, 1989
4,820,742
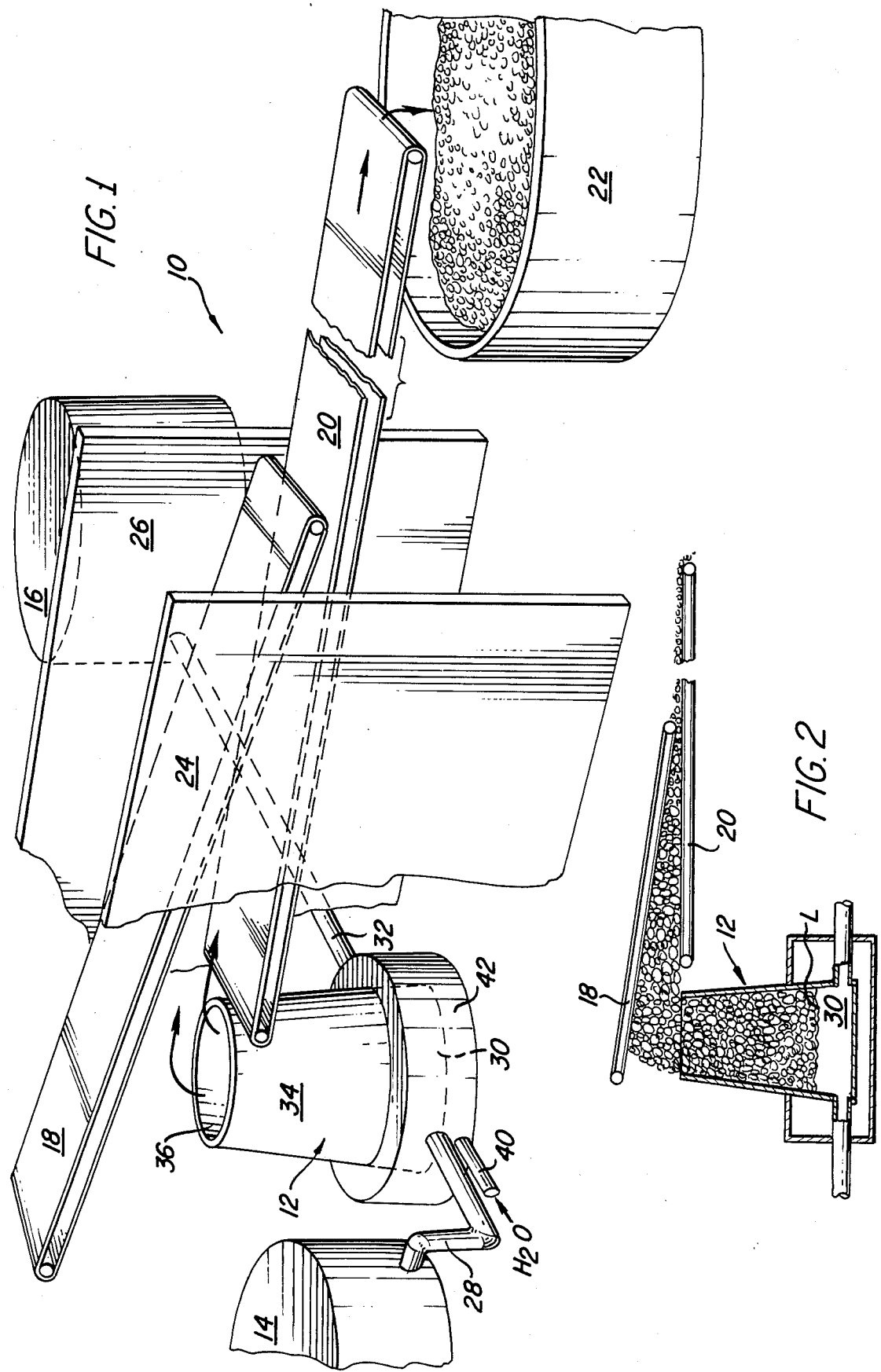

METHOD FOR CONTINUOUS MANUFACTURE OF SOLID WATER ABSORBING RESIN

CROSS REFERENCE TO RELATED APPLICATIONS

This application is a continuation of application Ser. No. 06/748,246 filed June 24, 1985, now abandoned.

FIELD OF THE INVENTION

The present invention relates to a continuous method and apparatus for manufacturing polyacrylate resins having improved water absorbing properties and more particularly to an improved process and apparatus for preparing, continuously, cross-linked polymers of acrylic acid and polyvinyl monomers.

BACKGROUND OF THE INVENTION

Water absorbing resins have found wide use in sanitary goods, hygenic goods, water retaining agents, dehydrating agents, sludge coagulants, thickening agents, condensation preventing agents and release control agents for various chemicals. Water absorbing resins heretofore known include hydrolysis products of starch-acrylonitrile graft polymers, carboxymethylcellulose, cross-linked polyacrylate products and other resins such as polyvinyl alcohol, polyethylene oxide and polyacrylonitrile resins. Of these water absorbing resins, the hydrolysis products of starch and acrylonitrile graft polymers have comparatively high ability to absorb water but require a cumbersome process for production and have the drawbacks of low heat resistance and decaying or decomposing easily due to the presence of starch.

One of the processes for polymerizing acrylic acid and acrylates is aqueous solution polymerization. The polymer obtained by this process is soluble in water and, therefore, is cross-linked to modify the polymer into a useful water absorbing resin. However, even if the modification is effected by reacting a cross-linking agent concurrently with or after aqueous solution polymerization, the resulting reaction product is in the form of a highly viscous aqueous solution of a gel containing absorbed water which is difficult to handle. Thus, the aqueous solution or gel must be dehydrated (dried) to obtain a water absorbing resin in the desired solid or powder form. It is nevertheless difficult to dry the reaction product efficiently by the usual rotary drum roller method or spray drying method because care must be taken to avoid excessive cross-linking which results from overheating during drying and insufficient drying results in reduced cross-linking density. Extreme difficulties are therefore encountered in preparing a product of a desired low water content and good water absorbing ability.

SUMMARY OF THE INVENTION

An object of the present invention is to provide a process and apparatus for preparing, continuously, a water absorbing cross-linked acrylate resin of low water content by aqueous solution polymerization without any additional dehydrating or drying step.

Another object of the present invention is to provide a process and apparatus for preparing, continuously, a cross-linked polyacrylate resin by polymerization of acrylic acid neutralized 70-100 mole percent, and a water-miscible or water soluble polyvinyl monomer in a combined concentration of 30 to 80 wt. % in water and initiating polymerization without external heating.

Another object of the present invention is to provide a process and apparatus for preparing, continuously, a cross-linked polyacrylate resin by co-polymerization of acrylic acid neutralized 70-100 mole percent, with acrylamide and a polyvinyl monomer in proportions of 0 to 30 mole percent acrylamide and 70-100 combined mole percent of neutralized acrylic acid and free acrylic acid.

Another object of the present invention is to provide a continous process and apparatus for producing a polyacrylate resin cross-linked with 0.2 weight percent to 0.6 weight percent based on the weight of monomers, of a water-miscible or water-soluble polyvinyl monomer cross-linking agent to achieve a "dry feel" to the resin after significant water absorption.

Still another object of the present invention is to provide a continuous process and apparatus for producing a polyacrylate resin wherein a combination of neutralizing agents are used to neutralize acrylic acid 70-100 mole percent, wherein one or more neutralizing agents reacts exothermically with acrylic acid and one or more neutralizing agents reacts endothermically with acrylic acid to avoid overheating of the monomer reactants.

In brief, the present invention is directed to a process and apparatus for preparing, continuously, water absorbing, cross-linked acrylate resins by aqueous polymerization of (A) acrylic acid neutralized 70 to 100 mole percent for example with ammonia, and/or caustic alkali and/or an amine; with (B) acrylamide in a mole ratio of 70 to 100 mole percent (A) to 30:0 mole percent (B); and (C) a water miscible or a water soluble polyvinyl monomer in an amount of 0.001 to 0.3 weight percent based on the total weight of (A) and (B). To achieve the full advantage of the present invention the monomer concentration is at least 50 wt. % of the aqueous solution. A "dry feel" is obtained at a polyvinyl monomer concentration of at least 0.2 wt. percent of the aqueous solution.

In accordance with the present invention, a heated aqueous solution comprising (A) acrylic acid neutralized 70 to 100 mole percent for example with ammonia, and/or caustic alkali and/or an amine; and (B) a water-miscible to water-soluble polyvinyl monomer, water and, when desired, an organic solvent having a boiling point of 40° to 150° C., and having a combined monomer concentration of (A) plug (B) of 30 to 80 wt. % is subjected to continuous polymerization in the presence of a polymerization initiator without external heating while allowing water to evaporate off.

BRIEF DESCRIPTION OF THE DRAWING

FIG. 1 is a perspective view of the apparatus of the present invention;

FIG. 2 is a cross-sectional view of the reaction chamber of the apparatus of the present invention.

DETAILED DESCRIPTION OF THE INVENTION

In accordance with the present invention a cross-linked polyacrylate resin is prepared by aqueous solution polymerization while dehydrating or drying the reaction product during polymerization by utilizing the exothermic heat from the polymerization and cross-linking reactions for drying.

It has been found that acrylic acid neutralized in the range of 70 to 100 mole percent will polymerize and cross-linked rapidly with a polyvinyl monomer cross-linking agent to drive away excess water leaving a solid water absorbing resin having a desired degree of polymerization as well as new and unexpected water absorbing capacity. One or more polymerization catalysts or initiators can be added to the aqueous monomer mixture to aid in polymerization.

According to the present invention, a hot aqueous solution is prepared first which comprises acrylic acid neutralized 70 to 100 mole percent, a water-miscible or water-soluble polyvinyl monomer, water and, when desired, an organic solvent having a boiling point of 40° to 150° C., and which contains the acrylate monomer and the polyvinyl monomer in a combined concentration of 30 to 80 wt. %. To achieve the full advantage of the present invention, the acrylate and polyvinyl monomers are present in a combined concentration of less than 70 weight percent of the monomer solution. In accordance with another important embodiment of the present invention, the combined concentration of the acrylate and polyvinyl monomers is less than 55 weight percent of the monomer solution. The concentration of the monomers is deliberately determined considering the state of the solution (i.e. as to whether or not the monomers can be completely dissolved in water), ease of the reaction of the monomers, escape of the monomers due to the scattering during the reaction, etc. The aqueous solution can be prepared easily usually by placing acrylic acid, a strong alkali such as potassium hydroxide and/or ammonium hydroxide or a basic amine for neutralizing the acid and the polyvinyl monomer into water in such amounts that the resulting solution has the above-mentioned monomer concentration. To dissolve the monomers thoroughly, the mixture can be heated to an elevated temperature. Any strongly basic alkali metal compound can be used for neutralization of the acrylic acid, such as potassium hydroxide, sodium hydroxide, lithium hydroxide, cesium hydroxide, potassium carbonate or sodium carbonate. Although it is desirable to use the neutralizing agent usually in an amount sufficient to neutralize acrylic acid 100 mol %, there is no particular need to neutralize the acid 100% insofar as the neutralizing agent, e.g., hydroxide, is used in such an amount as to achieve not less than about 70% neutralization. Accordingly the aqueous solution may contain up to about 30% of free acrylic acid. However, a large quantity of free acrylic acid, if present in the aqueous solution, is likely to partly splash out of the system to result in a loss during the reaction, leading to a reduced degree of polymerization. Use of an excessive amount of the neutralizing agent will not raise any particular problem, but the excess does not participate in the polymerization reaction and is therefore useless.

In accordance with another important features of the present invention, a combination of neutralizing agents, one which reacts exothermically with acrylic acid, e.g., a basic ammonium compound such as ammonium carbonate and/or ammonium hydroxide, and one which reacts endothermically with acrylic acid, e.g., potassium hydroxide, are used to maintain the monomer reactants at a proper reaction temperature without the necessity of cooling the reaction vessel.

We have also found that when the aqueous solution further contains an organic solvent having a boiling point of 40° to 150° C., the temperature of the aqueous solution is controllable with great ease and the resulting cross-linked resin has remarkably improved ability to absorb water at an initial rate.

When incorporating an organic solvent according to the invention, the aqueous monomer solution has a solidifying point which is about 10° to about 20° C. lower than otherwise. This increases the allowable range of temperature control at least about 3 times. The organic solvent used is vigorously evaporated along with water by the heat of polymerization of the monomer. Since the latent heat of the evaporation is considerably smaller than that of water, the organic solvent functions as a blowing agent in the polymerization reaction system, consequently rendering the resulting resin porous. The resin exhibits about 2 to about 5 times higher initial rate of water absorption than the one obtained without using the organic solvent while possessing high water absorbing ability.

Thus, the organic solvent, when added to the aqueous monomer solution, produces improved effects without in any way impairing the advantages resulting from the use of the monomer solution.

Examples of organic solvents to be used in the invention when desired and having a boiling point of 40° to 150° C. are methanol, ethanol, propanol and like alcohol solvents, acetone, methyl ethyl ketone and like detone solvents, cyclohexane, n-hexane, n-heptane and like hydrocarbon solvents, benzene, toluene and like aromatic hydrocarbon solvents, and tetrahydrofuran and like furan solvents. These solvents may be used singly or in admixture. The solvent is used in an amount of 0.5 to 15 wt. %, preferably 1 to 10 wt. %, based on the combined amount of the monomers. With less than 0.5 wt. % of the solvent present, a sufficient blowing action will not take place, while the solidifying point of the monomer solution will not lower greatly. Conversely if more than 15 wt. % of the solvent isused, the resulting resin is likely to exhibit reduced water absorbing ability although achieving a high initial rate of water absorption. Moreover the monomers are likely to separate out, hence objectionable. Because the monomer solution is heated prior to polymerization and further because the organic solvent evaporates along with water, the boiling point of the solvent is more preferably in the range of 55° to 120° C.

In accordance with the present invention, acrylic acid neutralized 70–100 mole percent is mixed with a water-miscible or water-soluble polyvinyl monomer in an aqueous solution at a temperature of about 20° to 100° C. and continuously fed to a reaction chamber through one reaction chamber inlet. The solution is subjected to a polymerization reaction and a cross-linking reaction by the continuous addition of a polymerization initiator through another reaction chamber inlet. The polymerization reaction proceeds sufficiently within a very short period of time and if the monomer concentration is at least 30 percent by weight of the aqueous monomer mixture, the heat of the polymerization and cross-linking reactions will evaporate water rapidly from the reaction product as it travels upwardly from an upper surface of the monomer solution onto a conveyor or other means to remove the reaction product (resin) from the reaction vessel to form a dry solid (less than 15 percent by weight water) water absorbing resin without the need for any subsequent drying step. The solid can be easily pulverized into a powder suitable for any desired use.

According to the continuous process of the invention, a hot, i.e. at least 25° C., aqueous solution is prepared first including acrylic acid neutralized 70 to 100 mole percent, optionally acrylamide, a water-miscible or water-soluble polyvinyl monomer, and water in a first reactant storage vessel. A reacting initiator is stored in a second reactant storage vessel so that the reactants from both vessels are fed simultaneously into a lower portion (below a continously maintained liquid level) in the reaction vessel. The aqueous solution can be prepared easily by placing (A) acrylic acid, and an amine, and/or a caustic alkali and/or ammonia for neutralizing the acid; (B) acrylamide (0–30 mole percent); and (C) a polyvinyl monomer into water to form a mixed monomer solution. To dissolve the monomers thoroughly, the mixture can be heated to an elevated temperature up to the boiling point of water i.e. 100° C.

The polyvinyl monomer to be used in both embodiments of the invention should be miscible with or soluble in water so that the monomer will be uniformly dissolved or dispersed in the aqueous solution of the monomer mixture. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

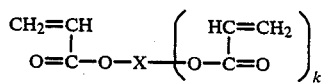

Formula (I)

wherein x is ethylene, propylene, trimethylene, hexamethylene, 2-hydroxypropylene, $(CH_2CH_2O)_nCH_2CH_2-$ or

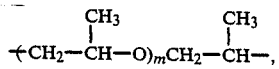

n and m are each an integer of from 5 to 40, and k is 1 or 2.

The compounds of the formula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid. Formula (II):

wherein l is 2 or 3.

The compounds of the formula (II) are obtained by reacting polyalkylene polyamines, such as diethylenetriamine and triethylenetetramine, with acrylic acid.

The polyvinyl monomer is used in an amount of about 0.001 to 0.3 wt. % of the amount of acrylic monomers in the aqueous monomer mixture. In accordance with an important embodiment of the present invention, the polyvinyl monomer should be present in the aqueous solution in an amount of at least 0.2 wt. % based on the total weight of monomers to provide a resin sufficiently cross-linked to have a "dry feel" after significant water-absorption. If the polyvinyl monomer is included in the aqueous solution in an amount of 0.2 to 0.6 weight percent based on the weight of neutralized acrylic acid and polyvinyl monomers, the resulting polymer will have an exceedingly "dry feel" on absorption of water.

The aqueous mixed monomer solution is heated and thereafter fed continuously to the reaction vessel simultaneously with a reaction initiator fed through a separate inlet conduit for polymerization and cross-linking reactions in the reaction vessel. Although the temperature of the aqueous mixed monomer solution is not particularly limited since the mixed monomer solution is initiated into polymerization by the addition of the initiator, the temperature is usually about 50° to about 85° C., preferably about 60° to about 75° C. Various polymerization initiators are usable which are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo initiators including azobis-isobutyronitrile, 4-t-butylazo-4'-cyanovaleric acid, 4,4'-azobis(4-cyanovaleric acid) and 2,2'-azobis(2-amidinopropane)-hydrochloric acid salt; trimethylolpropane triacylate, and the like. These initiators can be used singly or in a suitable combination. Of these, especially preferable are a redox initiator composed of ammonium persulfate and sodium hydrogensulfite, and azo initiators such a azobisisobutyronitrile and 2,2'-azobis(2-amidinopropane)-hydrochloric acid. These initiators are advantageously used usually in the form of an aqueous solution but can be used as diluted with a suitable solvent. The initiator is used in a usual amount, i.e. in an amount, calculated as solids, of about 0.1 to about 10%, preferably about 0.5 to about 5%, of the combined weight of the monomers, namely acrylate (and free acrylic acid), acrylamide, and polyvinyl monomer. Depending on the amount and kind of the initiator, the initiator is usable together with isopropyl alcohol, alkylmercaptan or other chain transfer agents to control the molecular weight of the polyacrylate to be obtained.

By the continuous addition of the polymerization initiator, the mixed monomer solution is subjected to continuous polymerization in a reaction chamber of the reaction vessel with evaporation of water without heating the system from outside. More advantageously, the reaction is carried out by admixing a predetermined amount of the initiator or an aqueous solution thereof with the mixed monomer solution and causing the resulting mixture to flow down onto and spread over a traveling conveyor belt. The initiator can be added to the mixed monomer solution as it is poured onto the conveyor belt.

The polymerization proceeds rapidly after admixing the initiator with the mixed monomer solution and is completed within a short period of time, usually in about 30 seconds to about 10 minutes. The reaction is exothermic, so that the reaction system is rapidly heated from a reaction temperature of about 70° C. to about 100° to about 130° C. by the heat of polymerization. Consequently, particularly where the least 50 percent by weight, the water evaporates from the system rapidly to give a relatively dry, solid polymer of low water content without resorting to any external heating. The water content of the polymer is usually up to about 15%, and generally about 8 to 12% by weight as recovered. Subsequently, the dry solid polymer can be made into the desired powder easily by a usual method, for example by pulverization, without a drying step.

In accordance with another important feature of the present invention, polystyrene and/or methylcellulose can be added to the mixed monomer solution in an amount of 0.5 to about 10 percent based on the total weight of monomers in the mixed monomer solution to increase the porosity and water absorbing capacity of the polymers. It has been found, quite surprisingly, the polystyrene and methylcellulose will substantially increase the water absorbing capacity of the resin described herein. To achieve the full advantage of the present invention, the polystyrene and methylcellulose should be added in an average grain size of less than or equal to 5 micrometers.

The powder thus obtained has outstanding water absorbing ability and is useful for sanitary goods, paper diaper, disposable diaper and like hygenic goods, agricultural or horticultural water retaining agents, industrial dehydrating agents, sludge coagulants, thickening agents, condensation preventing agents for building materials, release control agents for chemicals and various other applications.

The present invention will be described in greater detail with reference to the drawing and the following examples.

Referring now to the drawing, and initially to FIG. 1, there is illustrated apparatus for the continuous manufacture of water absorbing resin, generally designated by reference numeral 10. The apparatus 10 includes a reaction vessel, generally designated 12, a mixed monomer solution storage vessel 14, a polymerization initiator storage vessel 16, an upper reaction product conveyor belt 18, a lower reaction product conveyor belt 20, and a dry cured resin holding vessel 22. If desired, retaining walls 24 and 26 are provided between the two conveyor belts to retain the water absorbing resin reaction product on the lower conveyor belt 20.

The mixed monomer solution is stored in storage vessel 14 and the polymerization initiator stored in the initiator storage vessel 16. The monomer solution is fed by gravity or otherwise through conduit 28 to a lower position (below the liquid surface) of a reaction chamber 30 of the reaction vessel 12 at a rate of, for example, 4 gallons per minute. Simultaneously, the polymerization initiator is fed at a rate of, for example, 0.2 gallons per minute by gravity or otherwise through conduit 32 to an opposite side of the reaction chamber, again at a lower portion (below a continuously maintained liquid level) to being polymerization. The reaction product forms from an upper surface of the reactant mixture (mixed monomer solution plus initiator) and travels upwardly through a truncated frustoconical cone shaped upper portion 34 of the reaction chamber 30 as a solid resin. The reaction product is sufficiently rigid to proceed upwardly from an upper annular edge 36 of the upper reaction chamber portion 34 until the resin meets the upper conveyor belt 18. The upper conveyor belt 18, driven in a counterclockwise direction, pushes the mass of reaction product to the right, as shown in FIG. 1, onto the lower conveyor belt 20 on which the resin cures and dries without the addition of external heat. A suitable drying or curing time for the resins produced in accordance with the following examples 1–4, is, for example, 30 minutes. The lower conveyor belt can be of a suitable length for complete curing, or final curing and drying can occur in resin holding vessel 22.

EXAMPLE 1

To deionized water in vessel 14 are added, wherein percents are weight percents based on the total weight of the monomer solution formed, 58.81% acrylic acid first, then 11.76% potassium hydroxide and 11.76% ammonium carbonate and 14.70% ammonium hydroxide serving as neutralizing agents. Thereafter 0.03% of N,N-methylenebisacrylamide as a polyvinyl monomer is added to prepare an aqueous solution of potassium acrylate and ammonium acrylate in 2.79% of water having a neutralization degree of about 90% and a combined monomer concentration of 58.85 wt. %. The monomer solution is stored in storage vessel 14 until the polymer solution process begins by feeding polymerization initiator from vessel 16 simultaneously with monomer solution from vessel 14 into the reaction chamber 30 of the reaction vessel 34.

The aqueous solution is maintained at 70° C., and with the solution in reaction chamber 30 are continuously admixed to maintain a concentration of 0.15% of 2,2-azobis-(2-amidino-propane)hydrochloric acid. The final solution is as follows:

| CHEMICALS | |
|---|---|
| ACRYLIC ACID | 58.81% |
| POTASSIUM HYDROXIDE | 11.76% |
| AMMONIUM CARBONATE | 11.76% |
| N,N—METHYLENEBISACRYLAMIDE | 0.03% |
| POLYMERIZATION INITIATOR | 0.15% |
| AMMONIUM HYDROXIDE | 14.70% |
| $H_2O$ | 2.79% |
| TOTAL | 100.00 |

The polymer is allowed to complete curing for about 30 minutes at ambient temperature to give a dry solid mass of cross-linked potassium polyacrylate and ammonium acrylate product having a water content of 11% and a residual monomer concentration of 1200 ppm. The resin is made into a powder by a pulverizer (not shown).

EXAMPLES 2 TO 4

Polymers are prepared in the same manner as in Example 1 with the exception of varying, at least one of the combined concentration of monomers, the amount of polyvinyl monomer (N,N-methylenebisacrylamide), the kind and amount (degree of neutralization) of neutralizing agent, and the amounts, based on the combined amount of the monomers, of azo polymerization initiator. The following compositions were polymerized in the apparatus 10:

EXAMPLE 2

| ACRYLIC ACID | 56.80% |
|---|---|
| POTASSIUM HYDROXIDE | 14.77% |
| AMMONIUM CARBONATE | 11.36% |
| N,N—METHYLENEBISACRYLAMIDE | 0.03% |
| POLYMERIZATION INITIATOR | 0.14% |
| AMMONIUM HYDROXIDE | 14.20% |
| $H_2O$ | 2.70% |
| TOTAL | 100.00% |

EXAMPLE 3

| ACRYLIC ACID | 57.13% |

-continued

| | |
|---|---|
| POTASSIUM HYDROXIDE | 14.28% |
| AMMONIUM CARBONATE | 11.43% |
| N,N—METHYLENEBISACRYLAMIDE | 0.03% |
| POLYMERIZATION INITIATOR | 0.14% |
| AMMONIUM HYDROXIDE | 14.28% |
| H$_2$O | 2.71% |
| TOTAL | 100.00% |

EXAMPLE 4

| | |
|---|---|
| ACRYLIC ACID | 54.66% |
| POTASSIUM HYDROXIDE | 10.93% |
| AMMONIUM CARBONATE | |
| N,N—METHYLENEBISACRYLAMIDE | 0.11% |
| POLYMERIZATION INITIATOR | 0.41% |
| AMMONIUM HYDROXIDE | 30.61% |
| H$_2$O | 3.27% |
| TOTAL | 100.00% |

The amount of polyvinyl monomer listed as expressed in % by weight based on the combined amount of potassium acrylate, free acrylic acid and the polyvinyl monomer, and the concentration of initiator is expressed in % by weight based on the combined amount by weight (calculated as solids) of the monomers and the initiator, the same as hereinbefore.

EXAMPLE 5

To 22.2 gallons of deionized water in storage vessel 14 are added 72.1 gallons of acrylic acid first, then 49.5 gallons of potassium hydroxide having a purity of 85% and serving as a neutralizing agent, and thereafter 0.01 g of N,N-methylenebisacrylamide as a polyvinyl monomer to prepare an aqueous solution of potassium acrylate having a neutralization degree of 75% and a combined monomer concentration of 70 wt. % in storage vessel 14.

The aqueous solution is maintained at 70° C., and the solution from conduit 28 is fed at 4 gallons/ minute to reaction chamber 30 of reaction vessel 12. Simultaneously is fed at 0.2 gallons/minute until reactant level L is reached (FIG. 2). 18% aqueous solution of ammonium persulfate (0.5 wt. % based on the combined weight of the potassium acrylate, free acrylic acid and N,N-methylenebisacrylamide, the same as hereinafter). The mixture is fed into the reaction vessel 12. About 30 seconds thereafter, the mixture starts to polymerize, and the reactants are fed continuously to the reaction vessel 12. The maximum temperature of the mixture during the reaction is about 120° C.

The reaction gives a dry solid of cross-linking potassium polyacrylate product having a water content of 11% and a residual monomer concentration of 1200 ppm. The resin is made into a powder by a pulverizer. The powder has water absorbing ability of 450 as measured with use of deionized water or 60 as measured with 1% saline.

EXAMPLES 6 TO 9

Polymers are prepared in the same manner as in Example 5 with the exception of changing at least one of the amount of N,N-methylenebisacrylamide and the kind and amount of the polymerization initiator as listed in Table 1 below. Table 4 also shows the water content and water absorbing ability of each polymer obtained.

TABLE 1

| Ex. No. | Initiator Kind | Conc. | Amt. of Polyvinyl Monomer | Water Content | Water Absorbing Abililty | |
|---|---|---|---|---|---|---|
| | | | | | Deionized Water | 1% Saline |
| 6 | 2,2'-azobis-(2-amidino-propane)hydrochloric acid | 0.5 | 0.01 | 11 | 520 | 58 |
| 7 | 2,2'-azobis-(2-amidino-propane)hydrochloric acid | 0.5 | 0.02 | 12 | 610 | 65 |
| 8 | 2,2'-azobis-(2-amidino-propane)hydrochloric acid | 1.0 | 0.01 | 10 | 550 | 62 |
| 9 | 2,2'-azobis-(2-amidino-propane)hydrochloric acid | 1.0 | 0.02 | 11 | 580 | 63 |

EXAMPLES 10 TO 17

Polymers are prepared in the same manner as in Example 1 except that the compounds listed in Table 2 below are used as polyvinyl monomers in the listed amounts. Table 2 also shows the water content and water absorbing ability of each polymer obtained.

TABLE 2

| Ex. No. | Polyvinyl Monomer Kind | Amount | Water Content | Deionized Water Absorbing Ability |
|---|---|---|---|---|
| 10 | Ethylene glycol diallyl ester | 0.01 | 12 | 480 |
| 11 | Ethylene glycol diallyl ester | 0.02 | 13 | 430 |
| 12 | Diethylenetriamine-diacrylamid | 0.01 | 12 | 510 |
| 13 | Diethylenetriamine-diacrylamid | 0.02 | 12 | 450 |
| 14 | N,N—methylenebismethacrylamid | 0.01 | 9 | 520 |
| 15 | N,N—methylenebismethacrylamid | 0.05 | 11 | 390 |
| 16 | Polyethylene glycol diacrylate* | 0.01 | 10 | 500 |
| 17 | Polyethylene glycol | 0.05 | 11 | 430 |

TABLE 2-continued

| Ex. No. | Polyvinyl Monomer Kind | Amount | Water Content | Deionized Water Absorbing Ability |
|---|---|---|---|---|
| | diacrylate* | | | |

*Polyethylene glycol diacrylate used in Examples 20 and 21 is represented by the following formula:

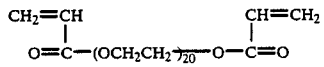

EXAMPLES 18 TO 21

Acrylic acid (72.1 g), 18.0 g of deionized water, 40.9 g of solid potassium hydroxide (water content 4%) and 5.2 g of one of the solvents (5 wt. % based on the monomers) listed in Table 3 are mixed together, and the mixture is maintained at 75° C. With the mixture is further admixed 4.0 g of 10% aqueous solution of 2,2'-azobis(2-amidinopropane)hydrochloric acid salt in reaction vessel 12. After about 1 minute, the reaction proceeds after which the reactants are continuously fed at the rate of example 1 into a lower portion of the reaction chamber 30. The maximum temperature of the mixture during the reaction is 130° to 135° C. If necessary, water coolant can be circulated through conduit 40, through cooling jacket 42 surrounding the lower portion of the reaction chamber 20 and through outlet 44 to cool the reactants.

The reaction gives a dry cross-linked potassium polyacrylate product, which is pulverized to a powder 20 to 100 mesh in particle size.

The same procedure as above is repeated with use of the other solvents. All the powders obtained have a water content of 4 to 6%.

A 0.1 g quantity of each of the powders is accurately measured out and the water absorbing ability of the powder is measured after immersing the powder in deionized water of 1% saline for 10 seconds, 30 seconds or 15 minutes. Table 3 shows the results.

EXAMPLE 22

An aqueous monomer solution is prepared in the same manner as in examples 17 to 21 with the exception of not using any organic solvent. The solution is thereafter subjected to polymerization in the same manner as in these examples to obtain a powder of dry solid. Table 3 also shows the test results obtained with this powder.

TABLE 3

| | Example No. | | | | |
|---|---|---|---|---|---|
| | 18 | 19 | 20 | 21 | 22 |
| | Organic Solvent | | | | |
| Water absorbing ability (times) | Acetone | Ethanol | Benzene | Tetrahydrofuran | (Water only) |
| 1% Saline | | | | | |
| 10 Sec. | 73 | 68 | 70 | 76 | 54 |
| 30 Sec. | 83 | 82 | 85 | 85 | 75 |
| 15 Min. | 97 | 93 | 94 | 96 | 96 |
| Deionized water | | | | | |
| 10 Sec. | 620 | 690 | 600 | 690 | 300 |
| 30 Sec. | 900 | 910 | 880 | 920 | 750 |
| 15 Min. | 960 | 980 | 900 | 980 | 920 |

We claim:

1. A process for continuously preparing a solid water absorbing resin comprising mixing a monomer solution (A) acrylic acid neutralized 70-100 mole percent, wherein the neutralizing agent comprises a potassium alkali; and (B) a water-miscible to water-soluble polyvinyl monomer in a combined concentration of at least 30 wt. % to 80 wt. %; with water to form a mixed monomer solution wherein the monomers of the mixed monomer solution consist essentially of (A) and (B) and initiating polymerization of monomers (A) and (B) by simultaneously feeding the mixed monomer solution and a polymerization initiator each through a reaction chamber inlet to begin polymerization in the reaction chamber; and continuously feeding the mixed solution and the polymerization initiator to the reaction chamber such that during polymerization, the exothermic heat of reaction is substantially the only heat energy used to accomplish polymerization, cross-linking and to drive off sufficient water to obtain a solid cross-linked resin having a water content of 15 percent by weight or less.

2. A process as defined in claim 1 wherein the continuous combined concentration of the liquid monomers (A) and (B) is at least 30 wt. % and less than 70 wt. %.

3. A process as defined in claim 1 wherein the mixed monomer solution has a temperature of 50° to 85° C. prior to polymerization.

4. A process as defined in claim 1 wherein monomer (B) is selected from the group consisting of N,N-methylenebisacrylamide and N,N-methylenebismethacrylamide.

5. A process as defined in claim 1 wherein the mixed monomer solution contains 1 to 10 wt. % of an organic solvent based on the weight of monomers (A) and (B).

6. A process as defined in claim 1 wherein the mixed monomer solution further contains an organic solvent having a boiling point of 40° to 150° C.

* * * * *